(12) United States Patent
Chaiken et al.

(10) Patent No.: US 6,377,828 B1
(45) Date of Patent: Apr. 23, 2002

(54) METHOD FOR NON-INVASIVE MEASUREMENT OF AN ANALYTE

(75) Inventors: Joseph Chaiken, Fayetteville, NY (US); Charles M. Peterson, Potomac, MD (US)

(73) Assignee: LighTouch Medical, Inc., New Hope, PA (US)

( * ) Notice: Subject to any disclaimer, the term of this patent is extended or adjusted under 35 U.S.C. 154(b) by 0 days.

(21) Appl. No.: 09/480,375

(22) Filed: Jan. 10, 2000

Related U.S. Application Data (63) Continuation of application No. 09/191,478, filed on Nov. 12, 1998, now Pat. No. 6,044,285.
(60) Provisional application No. 60/065,180, filed on Nov. 12, 1997.

(51) Int. Cl.[7] ................................. A61B 5/00
(52) U.S. Cl. ................. 600/316; 600/322; 356/301
(58) Field of Search .................. 600/310, 316, 600/322, 476; 356/39, 301

(56) References Cited

U.S. PATENT DOCUMENTS

| | | |
|---|---|---|
| 4,169,676 A | 10/1979 | Kaiser |
| 4,427,889 A | 1/1984 | Müller |
| 4,655,225 A | 4/1987 | Dähne |

(List continued on next page.)

FOREIGN PATENT DOCUMENTS

| | | |
|---|---|---|
| EP | 0 587 008 A1 | 3/1994 |
| EP | 0 637 742 A1 | 2/1995 |
| EP | 0 776 628 A2 | 6/1997 |
| WO | WO 88/06726 | 9/1988 |
| WO | WO 92/15008 | 9/1992 |
| WO | WO 97/13448 | 4/1997 |
| WO | WO 97/20495 | 6/1997 |

OTHER PUBLICATIONS

Anderson, R.R. et al., "The Optics of Human Skin," The Journal of Investigative Dermatology, vol. 77, No. 1, 1981, pp. 13–19.

Berger, A.J. et al., "Rapid, Noninvasive Concentration Measurements of Aqueous Biological Analytes by Near–Infrared Raman Spectroscopy," Applied Optics, vol. 35, No. 1, Jan. 1, 1996, pp. 209–212.

(List continued on next page.)

*Primary Examiner*—Eric F. Winakur
(74) *Attorney, Agent, or Firm*—Gates & Cooper LLP

(57) ABSTRACT

Disclosed is a method and apparatus for measuring an analyte in a tissue of a subject. The method comprises contacting the tissue with electromagnetic radiation having a first excitation wavelength, wherein the first excitation wavelength is substantially equal to an absorption wavelength of a temperature probe within the tissue. The temperature probe and the analyte are sufficiently proximate to one another that energy deposited into one by absorption of radiation is transferred to the other. The Raman spectra emitted by the tissue are collected and analyzed to determine a concentration of analyte present in the tissue. The analysis can comprise measuring the Raman spectra associated with the temperature probe. In addition, the method can include simultaneously contacting the tissue with electromagnetic radiation having the first excitation wavelength and with electromagnetic radiation having a second excitation wavelength, wherein the second excitation wavelength is substantially equal to an absorption wavelength of the analyte. The analysis comprises comparing the spectra emitted in response to the first excitation wavelength in the presence and in the absence of the second excitation wavelength. In another embodiment, the analysis comprises measuring the anti-Stokes component of the Raman spectra associated with the analyte. The method provides a non-invasive measurement of blood glucose, using hemoglobin as the temperature probe.

19 Claims, 2 Drawing Sheets

U.S. PATENT DOCUMENTS

| | | |
|---|---|---|
| 4,975,581 A | 12/1990 | Robinson et al. |
| 5,086,229 A | 2/1992 | Rosenthal et al. |
| 5,243,983 A | 9/1993 | Tarr et al. |
| 5,370,114 A | 12/1994 | Wong et al. |
| 5,372,135 A | 12/1994 | Mendelson et al. |
| 5,553,616 A | 9/1996 | Ham et al. |
| 5,553,617 A | 9/1996 | Barkenhagen |
| 5,582,168 A | 12/1996 | Samuels et al. |
| 5,601,079 A | 2/1997 | Wong et al. |
| 5,615,673 A | 4/1997 | Berger et al. |

OTHER PUBLICATIONS

Bhandare, P. et al., "Multivariate Determination of Glucose in Whole Blood Using Partial Least–Squares and Artificial Neural Networks Based on Mid–Infrared Spectroscopy," Applied Spectroscopy, vol. 47, No. 8, 1993, pp. 1214–1921.

Dou, X. et al., "Biological Applications of Anti–Stokes Raman Spectroscopy: Quantitative Analysis of Glucose in Plasma and Serum by a Highly Sensitive Multichannel Raman Spectrometer," Applied Spectroscopy, vol. 50, No. 10, 1996, pp. 1301–1306.

Robinson, M.R. et al., "Noninvasive Glucose Monitoring in Diabetic Patients: A Preliminary Evaluation," Clinical Chemistry, vol. 38, No. 9, 1992, pp. 1616–1622.

Wang, S.Y. et al., "Analysis of Metabolites in Aqueous Solutions by Using Laser Raman Spectoscopy," Applied Optics, vol. 32, No. 6, Feb. 20, 1993, pp. 925–929.

METHOD FOR NON-INVASIVE MEASUREMENT OF AN ANALYTE

This application is a continuation of U.S. patent application Ser. No. 09/191,478, filed Nov. 12, 1998, now U.S. Pat. No. 6,044,285, issued Mar. 28, 2000, which application claims the benefit of U.S. provisional patent appliation Ser. No. 60/065,180, filed on Nov. 12, 1997, the entire contents of which are hereby incorporated by reference into this application.

Throughout this application various publications are referenced. The disclosures of these publications in their entireties are hereby incorporated by reference into this application in order to more fully describe the state of the art to which this invention pertains.

TECHNICAL FIELD OF INVENTION

The invention relates to a method and apparatus for measuring an analyte in blood and other tissue. The method employs Raman spectroscopy wherein a temperature probe within the tissue is excited with electromagnetic radiation. The method results in enhanced spectral information related to concentration of the analyte.

BACKGROUND OF THE INVENTION

There has long been considerable interest in the non-invasive monitoring of body chemistry. There are 16 million American diabetics, all of whom would benefit from a method for non-invasive measurement of blood glucose levels. Using currently accepted methods for measuring blood glucose levels, many diabetics must give blood five to seven times per day to adequately monitor their insulin requirements. With a non-invasive blood glucose measurement, closer control could be imposed and the continuing damage, impairment and costs caused by diabetes could be minimized.

Blood oximetry is an example of an application of electronic absorption spectroscopy to non-invasive monitoring of the equilibrium between oxygenated and deoxygenated blood (U.S. Pat. No. 5,615,673, issued Apr. 1, 1997). Similarly, vibrational spectroscopy is a reliable mode of quantitative and qualitative ex vivo analysis for complex mixtures, and there are reports of in vitro applications of this method to metabolically interesting analytes (S. Y. Wang et al., 1993, Analysis of metabolites in aqueous solution by using laser Raman spectroscopy, Applied Optics 32(6) :925–929; A. J. Berger et al., 1996, Rapid, noninvasive concentration measurements of aqueous biological analytes by near-infrared Raman spectroscopy, Applied Optics 35(1) :209–212). Infrared measures, such as vibrational absorption spectroscopy, have been applied to skin tissue, but with success limited by unavailability of suitable light sources and detectors at crucial wavelengths, and by heating of the tissue due to the absorption of incident radiation (U.S. Pat. No. 5,551,422, see also R. R. Anderson and J. A. Parrish, 1981, The Optics of Human Skin, J. Investigative Dermatology 77(1):13–19). Previous attempts to provide methods for non-invasive blood glucose monitoring are summarized in U.S. Pat. No. 5,553,616, issued on Sep. 10, 1996.

SUMMARY OF THE INVENTION

The invention provides a method and apparatus for measuring an analyte in a tissue of a subject. The method uses Raman spectroscopy and radiation with a wavelength selected to excite a temperature probe within the tissue. The temperature probe and the analyte are sufficiently proximate to one another that energy deposited into one by absorption of radiation is transferred to the other. This approach permits an enhancement of the signal-to-noise ratio in the emitted Raman spectra so that spectral changes associated with the concentration of analyte in the tissue can be observed and measured. The signal-to-noise ratio is improved by techniques that enhance the signal, reduce the noise, reduce background, and/or unravel spectral congestion. In one embodiment, excitation of the analyte in addition to the temperature probe allows one to measure analyte concentration by detecting the temperature increase effected in the temperature probe. In addition, measuring the anti-Stokes spectra emitted by the analyte following excitation of the temperature probe avoids background fluorescence. In preferred embodiments, the method comprises contacting the tissue with electromagnetic radiation having a first excitation wavelength, wherein the first excitation wavelength is substantially equal to an absorption wavelength of a temperature probe within the tissue. The Raman spectra emitted by the tissue are collected and analyzed to determine a concentration of analyte present in the tissue. In one embodiment, the analyzing comprises measuring the Raman spectra associated with the temperature probe. The method can further comprise simultaneously contacting the tissue with electromagnetic radiation having the first excitation wavelength and with electromagnetic radiation having a second excitation wavelength, wherein the second excitation wavelength is substantially equal to an absorption wavelength of the analyte, and wherein the analyzing comprises comparing the spectra emitted in response to the first excitation wavelength in the presence and in the absence of the second excitation wavelength.

In one embodiment, the concentration of analyte is determined in accordance with the following relationship:

$$C_A = \Delta T / (C_p I_A \epsilon_A \Delta t);$$

wherein $C_A$ is the concentration of analyte;
wherein $\Delta T$ is the temperature shift between the temperature, in Kelvin, associated with Raman scattering emitted by the temperature probe in response to the first and second excitation wavelengths, and the temperature associated with Raman scattering emitted by the temperature probe in response to the first excitation wavelength in the absence of the second excitation wavelength;
wherein $C_p$ is the heat capacity of the tissue; wherein $I_A$ is the intensity of the electromagnetic radiation of the second excitation wavelength;
wherein $\epsilon_A$ is the absorption coefficient for a molecule of analyte;
and wherein $\Delta t$ is the duration of contact with the second excitation wavelength.

In another embodiment, the analyzing comprises measuring the Raman spectra associated with the analyte. The Raman spectra can comprise anti-Stokes spectra.

The method can be performed while the tissue is replete with blood and while the tissue is depleted of blood. In this embodiment, the analyzing comprises determining the difference between the Raman spectra collected in the blood replete and blood depleted states.

Examples of a temperature probe include, but are not limited to, hemoglobin, carboxyhemoglobin, myoglobin, melanin, and bilirubin. Examples of an analyte include, but are not limited to, glucose, creatinine, pyruvate, drugs, blood gases and urea.

DETAILED DESCRIPTION

The invention disclosed herein provides a method and apparatus for measuring an analyte in blood or other tissue of a subject. The method can be performed non-invasively, and provides an improved signal-to-noise ratio over currently available non-invasive techniques. The signal-to-noise ratio is enhanced by techniques, which enhance the signal, reduce the noise, reduce background, and/or unravel spectral congestion. The method achieves the improved signal-to-noise ratio by using Raman spectroscopy and selecting incident wavelengths that excite temperature probes present in tissues of the body. A temperature probe is a component that is sufficiently proximate to an analyte of interest that energy deposited into either the temperature probe or the analyte by absorption of radiation is transferred to the other.

In one embodiment, excitation of the temperature probe is used to achieve resonance enhancement of the Raman spectrum of the temperature probe, which makes the Raman signal more detectable over background fluorescence. In this embodiment, the Raman scattering produced by the temperature probe in response to an excitation wavelength that is absorbed by the temperature probe is measured with and without coincident excitation with a wavelength that is absorbed by the analyte. The shift in Raman scattering created by exciting the analyte is indicative of the amount of analyte present in the tissue.

In another embodiment, interference from background fluorescence is reduced by enhancing the anti-Stokes component of the Raman spectrum of the analyte. In this embodiment, the Raman scattering produced by the analyte is analyzed following excitation with a wavelength that is absorbed by the temperature probe. The excitation of the temperature probe induces a temperature increase that enhances the anti-Stokes component of the Raman spectrum of the analyte.

Raman scattering is the term applied to the phenomenon whereby light that is scattered off a sample of matter is shifted in wavelength from the incident wavelength. The amount of wavelength shift depends on the vibrational motions the matter is capable of undergoing and this provides a sensitive measure of molecular structure. When the incident light is chosen to coincide with a wavelength the molecules of interest absorb, resonance Raman scattering occurs. The interaction between the incident radiation and the molecule is intensified to the extent that the degree of Raman scattering is a thousand to a million times more intense than if the incident light is chosen not to coincide with a molecular absorption. This means that when blue-green light is directed onto a sample of material containing blood hemoglobin absorbs blue-green light), it scatters 99.9% of the incident photons not absorbed by the sample, without a shift in wavelength of the photons. The other 0.1% of the photons are shifted in wavelength in ways which depend on the structure, local chemical and physical environment of the hemoglobin, vibrational motions of the hemoglobin molecules and on the temperature of the sample.

If another wavelength is used, such as a longer wavelength (e.g., 700 nm or longer) that does not correspond to a wavelength strongly absorbed by hemoglobin or another temperature probe, then the percentage of photons scattered with shifted wavelengths is about a thousand times smaller. That is, typically 99.9999% are scattered without any shift in wavelength when there is no resonance enhancement. Such an enhancement in the strength of Raman scattering is caused by the absorption of the wavelength of the incident light.

This means if a mixture of substances is exposed to an incident wavelength, then those components of the mixture having a resonance enhancement will dominate the production of scattered photons with a shifted wavelength, i.e., the Raman scattering. This is what occurs in blood when blue-green light is used as a probe due to the resonance enhancement of Raman scattering from hemoglobin. The blue to blue-green spectral range is only absorbed preferentially by hemoglobin among blood constituents, and so presents a special opportunity for blood based temperature methods. Hemoglobin is a general temperature probe which, in one example, can be used to detect the temperature rise due to infrared absorption by glucose, such as anhydrous D-glucose (DAG).

The co-localization of glucose and hemoglobin is advantageous. Temperature gradients are inevitable, so the closer the temperature probe to the site of absorption, the stronger the effect on the temperature probe. The temperature is obtained by measuring and comparing the amount of scattered radiation having shorter wavelengths than the incident light, referred to as anti-Stokes scattering, to the amount of light scattered having wavelengths longer than the incident beam, i.e., Stokes scattering. The ratio of the two intensities for a given wavelength shift is directly related to how one calculates an actual temperature. This effect allows one to measure the temperature of the hemoglobin, and the immediate surrounding region, in a completely non-invasive manner. Moreover, it is not necessary to determine the actual temperature. By detecting the change occurring in one or the other of the Stokes or anti-Stokes scattering, one can calibrate the relative change in Raman scattering to a known glucose concentration.

Definitions

All scientific and technical terms used in this application have meanings commonly used in the art unless otherwise specified. As used in this application, the following words or phrases have the meanings specified.

As used herein, "tissue" means any portion of an organ or system of the body, including, but not limited to, skin, capillary beds, blood, muscle, breast and brain.

As used herein, "temperature probe" refers to a component present in the same tissue as the analyte. When energy is deposited into either the temperature probe or the analyte by absorption of radiation, energy is transferred from one to the other.

As used herein, "Raman spectra associated with" a given component refers to those emitted Raman spectra which one skilled in the art would attribute to that component. One can determine which Raman spectra are attributable to a given component by irradiating that component in a relatively pure form, and collecting and analyzing the Raman spectra emitted by the component in the relative absence of other components.

As used herein, "blood replete" refers to a state in which blood flow through a tissue is unobstructed by, for example, vasoconstriction induced by cooling or the application of pressure. The blood replete state can be enhanced by conditions which increase vasodilation, such as warming.

As used herein, "blood depleted" refers to a state in which blood flow through a tissue is substantially restricted and blood volume is minimized. A blood depleted state can be achieved by, for example, cooling and/or applying pressure to the tissue. Pressure can be applied directly using static force, such as by applying a macroscopic object against the tissue (e.g., flat optical window, directed stream of gas), or in a dynamic manner, such as by applying ultrasonic or other frequency acoustic waves to the tissue.

Methods of the Invention

The invention provides a method of measuring an analyte in a tissue of a subject. In one embodiment, the method comprises contacting the tissue with electromagnetic radiation having a first excitation wavelength. The first excitation wavelength is substantially equal to an absorption wavelength of a temperature probe within the tissue. The temperature probe and the analyte are sufficiently proximate to one another that energy deposited into one by absorption of radiation is transferred to the other. Examples of a temperature probe include, but are not limited to, hemoglobin, carboxy-hemoglobin, myoglobin, melanin and bilirubin. Examples of an analyte include, but are not limited to, glucose, urea, creatinine, pyruvate, tyrosine, tryptophan, bicarbonate, electrolytes, lactic acid, drugs, and blood gases such as $O_2$, $CO_2$ and NO. In a preferred embodiment, the temperature probe is hemoglobin and the analyte is glucose. The method further comprises collecting the Raman spectra emitted by the tissue, and analyzing the collected spectra to determine the amount of analyte present in the tissue. In one embodiment, the analyzing comprises measuring the Raman spectra associated with the temperature probe.

Optionally, the method can further comprise contacting the tissue with electromagnetic radiation having a second excitation wavelength. The tissue is contacted with the first and second excitation wavelengths simultaneously. The second excitation wavelength is substantially equal to an absorption wavelength of the analyte, and the analyzing comprises comparing the spectra emitted in response to the first and second excitation wavelengths. Information about the analyte can then be derived from the effect of the second excitation wavelength on the emitted spectra as compared to the spectra emitted in response to the first excitation wavelength in the absence of the second excitation wavelength. The Raman spectra analyzed can include both Stokes and anti-Stokes spectra. In one embodiment, the analyzing comprises determining the concentration of analyte from a temperature shift effected in the temperature probe by the second excitation wavelength in accordance with the following relationship:

$$C_A = \Delta T / (C_p I_A \epsilon_A \Delta t);$$

wherein $C_A$ is the concentration of analyte;
wherein $\Delta T$ is the temperature shift between the temperature, in Kelvin, associated with Raman scattering emitted by the temperature probe in response to the first and second excitation wavelengths, and the temperature associated with Raman scattering emitted by the temperature probe in response to the first excitation wavelength in the absence of the second excitation wavelength;
wherein $C_p$ is the heat capacity of the tissue;
wherein $I_A$ is the intensity of the electromagnetic radiation of the second excitation wavelength;
wherein $\epsilon_A$ is the absorption coefficient for a molecule of analyte;
and wherein $\Delta t$ is the duration of contact with the second excitation wavelength.

In another embodiment, the analyzing comprises measuring the Raman spectra associated with the analyte. The Raman spectra analyzed can comprise anti-Stokes spectra, which are the Raman scattered spectra having wavelengths shorter than the excitation wavelength. The intensity of anti-Stokes scattering is very sensitive to the temperature of the sample. The higher the temperature, the greater the intensity of the anti-Stokes scattered light, at the expense of the Stokes scattered light. Measurements of either or both of the Stokes and anti-Stokes components can be used to obtain a signal that is proportional to the amount of analyte. Anti-Stokes components of the spectra, although typically weaker than Stokes components, are useful because they are less likely than the Stokes components to be obstructed by interfering background. Stokes features can be used, but are preferably avoided when fluorescence or other background radiation is problematic.

Tissue Modulation

In preferred embodiments, the method of the invention is performed in conjunction with tissue modulation. Tissue modulation, as used herein, refers to manipulating the tissue to which the method is applied so that measurements can be made in both blood replete and blood depleted states. The difference between measurements taken in the blood replete and blood depleted states provides a measure indicative of components in the blood while minimizing the effects of extraneous spectroscopic signals due to calluses, dirt, soap residue and other sources associated with the surrounding tissue. When tissue modulation is employed, the analyzing step includes determining the difference between the Raman spectra collected in the blood replete and blood depleted states.

In preferred embodiments, the tissue is blood, such as blood circulating in the capillary bed of the fingertip. Other tissues can be used, such as ear lobe, muscle, skin, breast or brain. The subject is preferably a vertebrate, such as a mammal, bird, reptile or fish. Examples of mammals include, but are not limited to, human, bovine, porcine, ovine, murine, equine, canine, and feline. In a most preferred embodiment, the subject is human.

The method can further include the step of determining blood volume in the tissue of interest. In this embodiment, the analyzing comprises determining the amount of analyte per unit of blood volume. Blood volume can be measured by contacting the tissue modulated region with light chosen to have a wavelength at an isosbestic point for the oxy-deoxyhemoglobin binary equilibrium, i.e. 805 nm or 580 nm. The amount of light that returns is directly related to the volume of blood in the contacted region.

$I_I$ is the intensity of isosbestic points wavelength radiation injected into the tissue in question. $I_R$ is the intensity of isoibestic points wavelength radiation returned from the tissue in question. The ratio, $I_R/I_I$, which normalizes for the variation in blood volume over successive applications of tissue modulation, will often be constant for a series of measurements that occur on the same region of tissue with the same lasers and detectors. Consequently, this factor can be left out in the equations that follow, and measurement of concentration can be in units of blood volume defined by $I_R/I_I$.

These units of blood volume (or other tissue volume) will also be evident in the units of $\epsilon$, so that the interrogated volume need not appear explicitly in the equations that relate a temperature rise to the intensity of the incident excitation, the concentration of the temperature probe, the heat capacity of the medium and the duration of exposure. The volume will be implicitly included in the numerical value of $\epsilon$, and can be either measured empirically or estimated from the known extinction coefficients of the relevant substances in in vitro settings. This is possible due to the objective of determining relative changes in analyte concentration. The spatial overlap between the blood volume interrogated region and the analyte interrogated region need only maintain relative constancy over the course of the measurements to provide sufficient precision in the estimate of temperature change and thereby analyte concentration. The regions would be expected to overlap considerably, although the different wavelengths used for different tasks would have different penetration depths. Given other measurement-related constraints, it is not necessary to achieve complete overlap.

In one embodiment, the first excitation wavelength is about 647 to about 400 nm. Preferably, the wavelength is about 550 to about 400 nm. In more preferred embodiments, the wavelength is about 588, 514, 473, 532 or 457 nm. The electromagnetic radiation to be used as the excitation wavelength in the method preferably has a bandwidth of about 0.03 nm to about 0.000003 nm. In one embodiment, the second excitation wavelength is about 0.98, about 1.42, about 1.89, about 2.15, or about 9 to about 11 $\mu$m.

In a preferred embodiment, the invention provides a method of measuring blood glucose concentration in a subject. The method comprises contacting tissue of the subject with electromagnetic radiation having a first excitation wavelength in the blue to blue-green range, and while the tissue of the subject is in a blood replete state. In one embodiment, the first excitation wavelength is about 550 to about 400 nm. The method further comprises collecting Raman spectra emitted by the tissue in response to the first excitation wavelength, wherein the Raman spectra comprise Stokes and anti-Stokes spectra. The collected spectra are then analyzed to determine the spectra associated with hemoglobin. The method further comprises contacting tissue of the subject with electromagnetic radiation having a second excitation wavelength of about 0.98, about 1.42, about 1.89, about 2.15, or about 9 to about 11 $\mu$m, and while the tissue of the subject is in a blood replete state. The tissue is contacted with the first and second excitation wavelengths simultaneously. The Raman spectra, including Stokes and anti-Stokes spectra, emitted by the tissue in response to the second excitation wavelength are collected and analyzed to determine the spectra associated with glucose. The above steps are also performed while the tissue is in a blood depleted state, either before, after or alternately with, performance of the steps while the tissue is in a blood replete state. The method further comprises determining the net spectra emitted in response to the first and second excitation wavelengths, wherein the net spectra comprise the difference between the spectra obtained in the blood replete state and the blood depleted state, and determining a first ratio of anti-Stokes to Stokes spectra emitted in response to the first excitation wavelength and a second ratio of anti-Stokes to Stokes spectra emitted in response to the second excitation wavelength. The second ratio is divided by the first ratio to obtain a value representative of the concentration of glucose.

In one embodiment, the analyzing comprises determining the concentration of glucose from a temperature shift effected in hemoglobin by the second excitation wavelength in accordance with the following relationship:

$$C_G = \Delta T / (C_p I_G \epsilon_G \Delta t);$$

wherein $C_G$ is the concentration of glucose;
wherein $\Delta T$ is the temperature shift between the temperature, in Kelvin, associated with Raman scattering emitted by hemoglobin in response to the first and second excitation wavelengths, and the temperature associated with Raman scattering emitted by hemoglobin in response to the first excitation wavelength in the absence of the second excitation wavelength;
wherein $C_p$ is the heat capacity of the tissue;
wherein $I_G$ is the intensity of the electromagnetic radiation of the second excitation wavelength;
wherein $\epsilon_G$ is the absorption coefficient for a molecule of glucose;
and wherein $\Delta t$ is the duration of contact with the second excitation wavelength.

In another preferred embodiment, the invention provides a method of measuring blood glucose in a subject. The method comprises contacting tissue of the subject with electromagnetic radiation having a first excitation wavelength in the blue to blue-green range, and while the tissue of the subject is in a blood replete state. In one embodiment, the wavelength is about 550 nm to about 400 nm. The method further comprises collecting Raman spectra, including anti-Stokes spectra emitted by the tissue, and analyzing the collected spectra to determine the spectra associated with glucose. The above steps are also performed while the tissue is in a blood depleted state, either before, after or alternately with, performance of the steps while the tissue is in a blood replete state. The method further comprises determining the net spectra emitted in response to the first excitation wavelength, wherein the net spectra comprise the difference between the spectra obtained in the blood replete state and the blood depleted state, to obtain a value representative of the concentration of glucose.

Limiting the analysis to the anti-Stokes portion of the emitted spectra eliminates much of the background found in the Stokes portion of the spectra.

Apparatus

Figure 1:
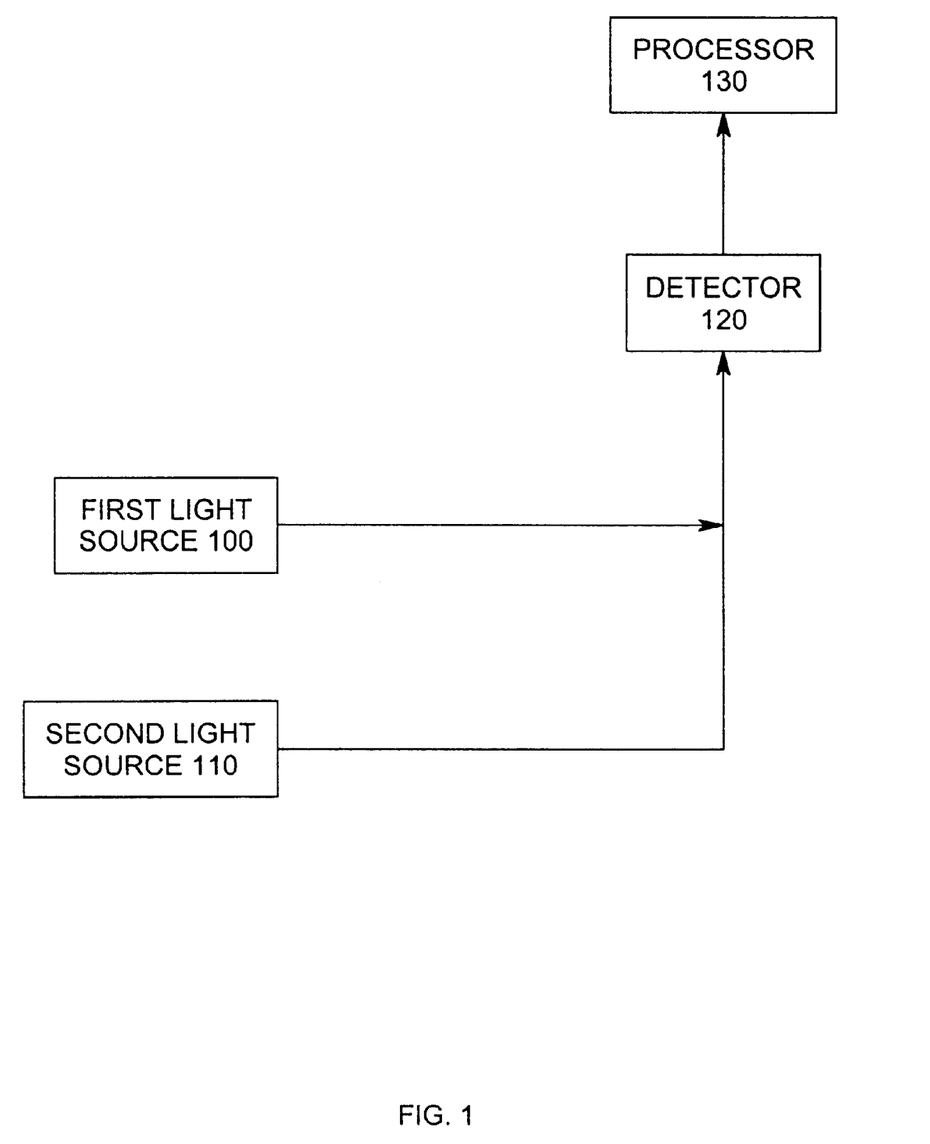
FIG. 1 is a block diagram representing one embodiment of an apparatus of the invention.

The invention provides an apparatus for measuring an analyte in a sample. The sample can be a tissue in a subject, including, for example, skin, muscle, capillary beds, blood, breast or brain. A diagram representing an apparatus of the invention is shown in FIG. 1. The apparatus comprises a first light source 100, a detector 120, and a signal processor 130. The apparatus is suitable for use with the methods of the invention disclosed herein. Suitable components and specific embodiments of the apparatus can be adapted from other Raman spectroscopy systems known in the art (see, e.g., U.S. Pat. Nos. 5,553,616; 5,510,894; 5,615,673; and 5,551,422).

The first light source 100 emits electromagnetic radiation having a first excitation wavelength, wherein the first excitation wavelength is substantially equal to an absorption wavelength of a temperature probe within the sample. Preferably, the light source is a laser. Examples of lasers suitable for use in producing the first excitation wavelength include, but are not limited to, external cavity diode lasers, $CO_2$ lasers and semiconductor lasers. In a preferred embodiment, the apparatus further comprises a second light source 110 that emits electromagnetic radiation having a second excitation wavelength that is substantially equal to an absorption wavelength of the analyte. Examples of lasers suitable for use in producing the second excitation wavelength include, but are not limited to, argon ion, krypton ion and frequency-doubled YAG lasers. In one embodiment, the first excitation wavelength is about 550 to about 400 nm, and the second excitation wavelength is about 0.98, 1.41, 1.89, 2.15, or about 9 to about 11 $\mu$m.

The detector 120 is a photosensitive device that is disposed to receive Raman spectra emitted by the sample. The detector 120 can include a wavelength selection device 210. In one embodiment, the wavelength selection device 210 is a wavelength selection spectrograph, preferably utilizing holographic transmission grating and charge coupled device (CCD) array detection. Scattered light can be pre-filtered prior to entering the spectrograph slit using a holographic notch filter. In one embodiment, the filter has a band blocking width of about 250 cm$^{-1}$ (or about 1 nm), centered at the corresponding excitation wavelength. In another embodiment, the wavelength selection device 210 is a single channel detector. Examples of a single channel detector include, but are not limited to, a photodiode such as an avalanche photodiode, and a photomultiplier tube. Light entering the single channel detector can be filtered, for example, using a single notch filter or dielectric stack. In preferred embodiments, the detector 120 is cooled using, for example, liquid nitrogen or another suitable cooling method known in the art. The detector 120 produces output signals representative of the Raman spectra scattered by the sample in response to irradiation with the first and/or second light sources 100, 110.

The processor 130 is coupled to receive the output signals produced by the detector 120. In one embodiment, the processor 130 is a computer coupled to receive the output signals produced by the detector. The computer processes the output signals to derive a value indicative of the concentration of analyte in the tissue from a comparison of output signals representative of the Raman spectra scattered in response to the first and second excitation wavelengths. In one embodiment, the computer processes the output signals in accordance with the following relationship:

$$C_A = \Delta T / (C_p I_A \epsilon_A \Delta t);$$

wherein $C_A$, $\Delta T$, $C_p$, $I_A$, $\epsilon_A$ and $\Delta t$ are as defined above.

Figure 2:
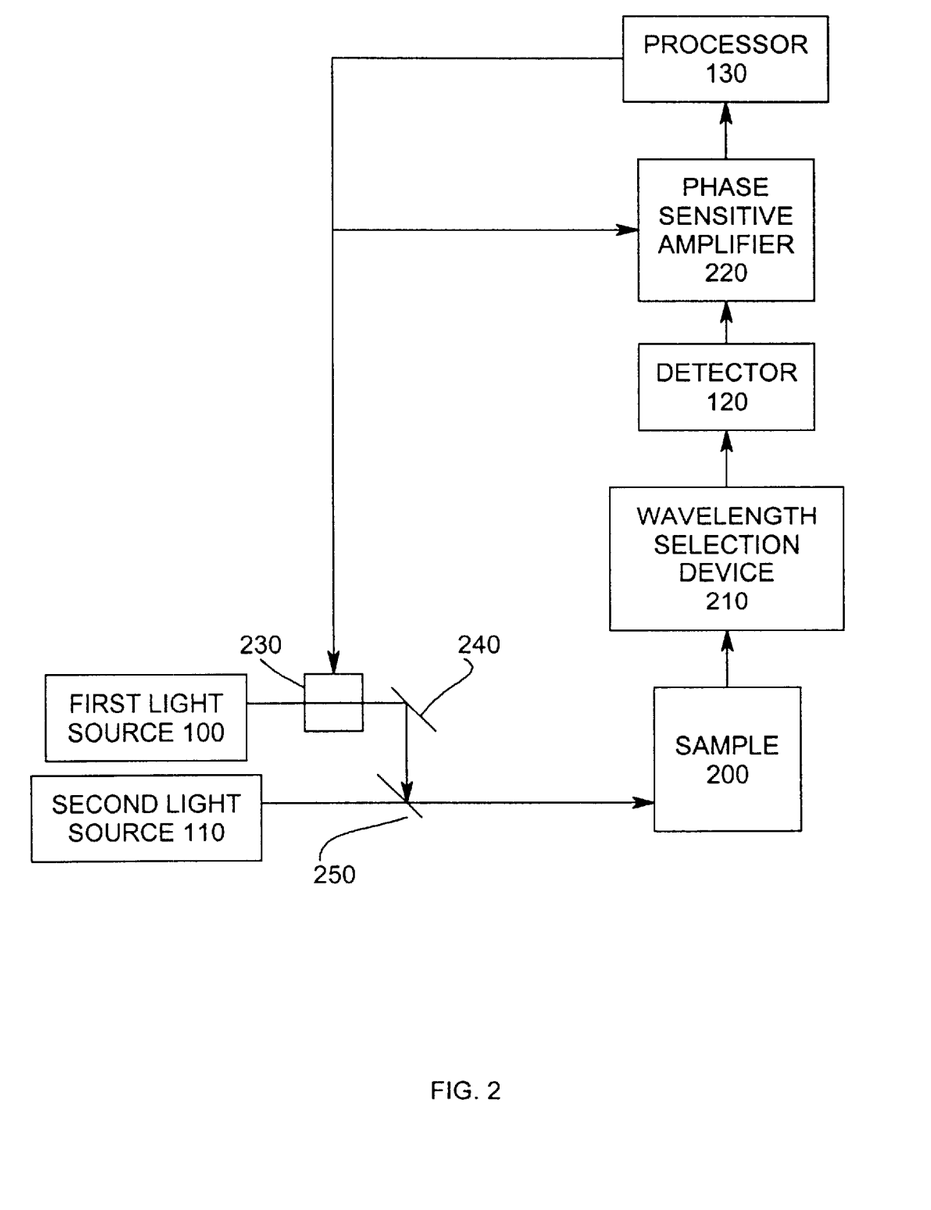
FIG. 2 is a block diagram representing a second embodiment of an apparatus of the invention.

Another embodiment of the apparatus is shown in FIG. 2. Light emitted by the first light source 100 passes through an amplitude modulator 230 to first and second reflectors 240, 250 such that the light joins the path of light emitted by the second light source 110. The light then irradiates the sample 200. Light scattered by the sample reaches a wavelength selection device 210 that includes a filter tuned to transmit a selected Raman feature. One such feature includes wavelengths of 1008 nm to 1029 nm for skin keratin excited with 785 nm. In one embodiment, the wavelength selection device 210 has a 250 µm slit and uses a holographic transmission grating.

The selected signal is then received by a detector 120. In one embodiment, the detector 120 is a charge coupled device (CCD) array, which can be cooled with liquid nitrogen. Alternatively, the detector 120 can comprise a single channel detector. The detector 120 optionally includes spatial characteristics, such as a quadrant spatial layout, allowing simultaneous use of spatial (Hadmaard/other/tissue modulation) encoding/modulation.

The signal then passes to a phase sensitive amplifier 220 that comprises a lock-in amplifier/gated integrator set to demodulate the signal stimulated by modulator 230. The processor 130 then takes analog demodulated signal from the phase sensitive amplifier 220 and performs digitization, storage and data processing. In addition, the processor 130 can provide synchronization with concurrent tissue modulation or spatial encoding.

Examples of temperature probes include, but are not limited to, hemoglobin, carboxyhemoglobin, myoglobin, melanin and bilirubin. Examples of analytes include, but are not limited to, glucose, urea, creatinine, pyruvate, tyrosine, tryptophan, bicarbonate, electrolytes, lactic acid, drugs and blood gases such as $O_2$, $CO_2$ and NO. In one embodiment, the temperature probe is hemoglobin and the analyte is glucose.

EXAMPLES

The following examples are presented to illustrate the present invention and to assist one of ordinary skill in making and using the same. The examples are not intended in any way to otherwise limit the scope of the invention.

Example 1

Use of Resonance Enhancement of Hemoglobin to Obtain an in Vivo Glucose Measurement For a given molecule, it is possible to identify various wavelengths of light, from the infrared to the ultraviolet parts of the electromagnetic spectrum, which would be preferentially absorbed, compared to the total absorption by all other components of the blood and tissues. Anhydrous d-glucose (DAG) has a molecular extinction coefficient at or near the 9–11 µm wavelength region which is significantly larger than that of most proteins, salts, fats and even water, comprising human tissues and blood. A number of sugars, partially phosphorylated sugars and other intermediates in sugar metabolism absorb at various wavelengths within the same wavelength range.

The concentrations of a majority of these sugars and near sugars are closely correlated with each other by the equilibria associated with sugar metabolism. Individual sugars and related components absorb infrared light at distinctly different wavelengths within and beyond the wavelength range mentioned above. It has not been possible, however, to detect this excitation using conventional means which rely on measurements directed to the same wavelength as that which is incident on the sample. For example, detection of backscattered light at the same wavelength, known as Rayleigh scattered radiation, is not selective since it contains contributions from the blood volume as well as the tissue. Either of these scattering centers can be sufficiently variable to render a nonselective, total power measurement meaningless.

Because absorption of light deposits energy into the illuminated region, it effects a rise in temperature. The amount of temperature rise is proportional to the number of photons absorbed, the heat capacity of the absorber and immediately surrounding region and the relative rates of energy absorption and energy conduction into the surrounding tissues and fluids. By measuring the temperature rise, on exposing a certain blood or tissue sample in vivo to radiation of an appropriate wavelength, one can detect the absorption of the absorbing species. Thus, the measurement of absorption of light, for example through absorption by DAG upon illumination by the correct specific wavelength(s), reduces to the problem of measuring the associated temperature rise. This example describes a simple, versatile method for obtaining non-invasive temperature measurements.

For the specific case of DAG, the method depends on obtaining measurements of Raman scattered radiation from the erythrocytes in which anhydrous d-glucose is localized. The technique can be applied to a variety of analytes and temperature probes. Free DAG can be found in blood in the cytoplasmic volume of the erythrocytes. Exposing the blood volume through the skin via the capillary beds to infrared radiation at the correct wavelength, (a specific wavelength in the 9–10 µm wavelength range for example), so that it will be preferentially absorbed by DAG, will cause the intraerythrocyte materials to increase in temperature. One substance in close proximity to the point of absorption, and thereby heated by the energy deposited into the DAG, is hemoglobin.

Blood volume can be measured by contacting the tissue modulated region with light chosen to have a wavelength at an isosbestic point for the oxy-eoxyhemoglobin binary equilibrium, i.e. 805 nm or 580 nm. The amount of light that returns is directly related to the volume of blood in the contacted region. $I_I$ is the intensity of isosbestic points wavelength radiation injected into the tissue in question. $I_R$ is the intensity of isosbestic points wavelength radiation returned from the tissue in question. The ratio, $I_R/I_I$, which normalizes for the variation in blood volume over successive applications of tissue modulation, will often be constant for a series of measurements that occur on the same region of tissue with the same lasers and detectors. Consequently, this factor is left out in the equations that follow and measurement of concentration will be in units of blood volume defined by $I_R/I_I$.

A normalizing factor relating the quality of the optical contact between the instrumental optical system and the tissue region of interest is obtained by contacting the region with a wavelength that is not absorbed by any component of the region, and detecting the amount of the light which returns. $I_N$ is the intensity of non-absorbed wavelength radiation injected into the tissue in question. $I_S$ is the intensity of non-absorbed wavelength radiation returned from the tissue in question. It should be pointed out that the ratio, $I_S/I_N$, which normalizes for the variation in blood volume over successive applications of tissue modulation, will often be constant for a series of measurements that occur on the same region of tissue with the same lasers and detectors. Consequently, this factor is left out in the equations that follow and measurement of concentration is in units of blood volume defined by $I_S/I_N$.

Step 1: During this step, there is no external pressure applied to the tissue being examined. A Raman spectrum, Stokes and anti-Stokes, is obtained by optically contacting the skin of a finger tip and the tissue/capillary bed below the skin with narrow spectral bandwidth light. The light that scatters due to the interaction of this "exciting" light with the tissue is collected and analyzed by wavelength. The exciting light is chosen so that the intensity of the Raman spectrum of hemoglobin is resonance enhanced.

The Stokes part of the Raman spectrum obtained during step 1 is referred to as $R_o(\lambda)_{s1}$. The anti-Stokes part of the Raman spectrum obtained during step 1 is referred to as $R_o(\lambda)_{as1}$.

The Raman scattered light, i.e. wavelength shifted light, has its origin in the interaction of the incident light, i.e. the exciting light, with the various chemical species in the mixture. In addition to any fluorescence the absorption may have induced, part of the Raman spectrum occurs at longer wavelengths than the incident light. This is called Stokes scattering. In contrast to fluorescence following the absorption of a single photon, another part of the Raman scattered light also can be observed at shorter wavelengths. This is called anti-Stokes scattering. The intensity of this scattering to shorter wavelengths is very sensitive to the temperature of the sample. The higher the temperature, the greater the intensity of the anti-Stokes scattered light at the expense of the Stokes scattered photons. The ordinary Raman scattering process, which involves the interaction of the vibrations of the molecules with the incident light, tends to produce one wavelength shifted photon of light for every $10^6$ incident photons. In contrast, ordinary fluorescence produces one photon for every $10^3$ incident photons.

Temperature

The following equation relates the intensity of a generic Stokes ($I_S$) and anti-Stokes ($I_{AS}$) components of a vibrational mode having frequency ($\upsilon$), to the temperature (T) of the system, the frequency ($\upsilon_0$) of the exciting radiation and q, the ratio of the detector response at the two wavelengths corresponding to $\upsilon_{AS}$ and $\upsilon_S$. h is Planck's constant and k is Boltzmann's constant.

$$I_{AS}/I_S = (\upsilon_{AS}-\upsilon_0)4/(\upsilon_S-\upsilon_0)^4 \; q \; \exp(h\upsilon/kT)$$

Glucose has a strong Raman feature at 200 cm$^{-1}$. A temperature rise of ≈12° C., which would occur on a transient basis, and is below the static temperature known to cause histological damage, would cause a 10% change in the ratio $I_{AS}/I_S$. The transient temperature rise due to absorption of radiation, $\Delta T$, is proportional to the total amount (energy) of radiation absorbed, $E_A$, and the net heat capacity of the medium, $C_p$. The heat capacity of human tissue is on the same order as water. Based on an irradiated volume on the order of microliters, absorbing only on the order of $10_0$–$10_1$ microjoules is sufficient to cause such a temperature rise. This amount of energy can be produced by $CO_2$ lasers in a bandpass around 9–10 µm in wavelength, which happens to be absorbed by glucose and a number of its immediate metabolic progeny. There are other wavelengths in the near-infrared spectral region, such as 980, 1410, 1890, 2150 nm, that are also thought to be selectively absorbed by glucose and are more conveniently produced using semiconductor lasers.

$$\Delta T = C_p E_A$$

The energy absorbed, within the irradiated volume, is proportional to the concentration of absorbing species, i.e. glucose molecules, $C_G$, the intensity of the radiation at the wavelength in question, and the absorption coefficient per such molecule. $E_A$ is expressed as:

$$E_A = C_G I_G \epsilon_G \Delta t$$

Glucose and hemoglobin tend to be spatially localized in the erythrocytes such that energy deposited into one by absorption of radiation will tend to be transferred to the other (and other components of the localized region), preferentially affecting the spectra of each. The energy absorbed is proportional to the intensity of the incident radiation, the duration ($\Delta t$) the absorbers are exposed, the concentration of absorbers (glucose, $C_G$), and the extinction coefficient of the absorbers at the wavelength of the incident radiation, e.g. $\epsilon_G$ for glucose.

Beer's Law applies to the absorption of radiation by tissue in the following relative sense. The effective pathlength for a particular wavelength can be held constant during the spectral interrogation, and the incident radiation can be maintained at a constant intensity. This is true, independent of the fact that light in tissue propagates in the multiple scattering limit (R. R. Anderson and J. A. Parrish, 1981, The Optics of Human Skin, J. Investigative Dermatology 77(1):13–19). In addition, the temporal synchronization of the various exposures and measurements can be held constant so the relative absorption is dependent only on the relative concentration of the absorbers. Thus the relative temperature change of the hemoglobin is dependent on the concentration of glucose.

Resonance Enhancement

There is a range of wavelengths spanning the blue-green part of the visible spectrum, and to a weaker extent even beyond the 600 nm range, which correspond to electronic absorption of the hemoglobin in erythrocytes. Excitation of Raman spectra of hemoglobin, either oxygenated or deoxyhemoglobin, using incident light in these ranges (particularly in the blue-green) results in as much as a $10^3$–$10^6$-fold enhancement of the Raman intensity. This enhancement is due to the electronic interaction intensifying the scattering process and it makes Raman spectroscopy a particularly sensitive probe of such molecules, particularly in the presence of a fluorescence background.

Step 2: During this step, there is no external pressure applied to the tissue being examined. Another resonance enhanced Raman spectrum, Stokes and anti-Stokes, is obtained by optically contacting the skin of a finger tip with narrow spectral bandwidth light. Simultaneously, the tissue is contacted with a light source having intensity $I_G$, capable of preferentially being absorbed by glucose over other species in the tissue/blood.

The Stokes part of the Raman spectrum obtained during step 2 is referred to as $R_o(\lambda)_{s2}$, and the anti-Stokes part of the Raman spectrum obtained during step 2 as $R_o(\lambda)_{as2}$.

Step 3: During this is step, external pressure is applied to the tissue being examined. A Raman spectrum, Stokes and anti-Stokes, is obtained by optically contacting the skin of a finger tip and the tissue/capillary bed below the skin with narrow spectral bandwidth light. The light that scatters due to the interaction of this "exciting" light with the tissue is collected and analyzed by wavelength. The exciting light is chosen so that the intensity of the Raman spectrum is resonance enhanced for the temperature probe.

The Stokes part of the Raman spectrum obtained during step 3 is referred to as $R_p(\lambda)_{s3}$, and the anti-Stokes part of the Raman spectrum obtained during step 3 as $R_p(\lambda)_{as3}$.

Step 4: During this step, external pressure is applied to the tissue being examined. Another resonance enhanced Raman spectrum, Stokes and anti-Stokes, is obtained by optically contacting the skin of a finger tip with narrow spectral bandwidth light. Simultaneously, the tissue is contacted with a light source of intensity, $I_G$, capable of preferentially being absorbed by glucose over other species in the tissue/blood.

The Stokes part of the Raman spectrum obtained during step 4 is referred to as $R_p(\lambda)_{s4}$, and the anti-Stokes part of the Raman spectrum obtained during step 4 as $R_p(\lambda)_{as4}$. Let:

$$(R_0(\lambda)_{as1} - R_p(\lambda)_{as3})/(R_0(\lambda)_{s1} - R_p(\lambda)_{s3}) \to A$$

$$(R_0(\lambda)_{as1} - R_p(\lambda)_{as3})/(R_0(\lambda)_{s1} - R_p(\lambda)_{s3}) = (v_{AS} - v_0)^4/(v_S - v_0)^4 q \exp(hv/kT_0).$$

Where $T_0$ corresponds to the temperature, in Kelvin, associated with the Raman scatterers without the preferential excitation of glucose.

Similarly, let:

$$(R_0(\lambda)_{as2} - R_p(\lambda)_{as4})/(R_0(\lambda)_{s2} - R_p(\lambda)_{s4}) \to B$$

$$(R_0(\lambda)_{as2} - R_p(\lambda)_{as4})/(R_0(\lambda)_{s2} - R_p(\lambda)_{s4}) = (v_{AS} - v_0)^4/(v_S - v_0)^4 q \exp(hv/kT_0).$$

Where T corresponds to the temperature, in Kelvin, associated with the Raman scatterers with the preferential excitation of glucose.

So that:

$$B/A = C \exp(\Delta T/TT_0)$$

$$\ln(B/A) = \ln(C) + (\Delta T/TT_0)$$

Thus the measured ratio B/A can be used in the following:

$$\Delta T = TT_0 \ln(B/A)$$

with $\Delta T = C_p E_A = C_p C_G I_G \epsilon_G \Delta t$ or $\Delta T/(C_p I_G \epsilon_G \Delta t) = C_G$.

It is possible to calculate the concentration of glucose, $C_G$, directly from the set of measurements, with many interfering influences dividing themselves out along the way.

Measurements of relative temperature rise can be empirically correlated with independently measured glucose concentrations. The above discussion demonstrates an algorithm and shows that there is a rigorous basis for empirically applying two variations of the method for noninvasive analyte quantitation.

Example 2

Use of Anti-Stokes Raman Spectra to Obtain an in Vivo Glucose Measurement

The strength of the anti-Stokes component of the glucose spectrum is dependent on the intensity of exciting radiation, which excites hemoglobin and heats glucose. The intensity of anti-Stokes scattering is very sensitive to the temperature of the sample. The higher the temperature, the greater the intensity of the anti-Stokes scattered light, at the expense of the Stokes scattered light. Anti-Stokes components of the spectra are useful because they are less likely than the Stokes components to be obstructed by interfering background. In this Example, an excitation wavelength that excites hemoglobin is used to heat glucose, thereby enhancing the anti-Stokes spectra associated with glucose.

Step 1: During this step. there is no external pressure applied to the tissue being examined. A Raman spectrum, Stokes and anti-Stokes, is obtained by optically contacting the skin of a finger tip and the tissue/capillary bed below the skin with narrow spectral bandwidth light. The light that scatters due to the interaction of this "exciting" light with the tissue is collected and analyzed by wavelength. The exciting light is chosen to have a wavelength that is absorbed by hemoglobin. The objective is to induce as little fluorescence as possible while injecting sufficient energy into the hemoglobin. This will heat the glucose in the immediate vicinity of the excited hemoglobin and cause the intensity of anti-Stokes features to be observed. Low frequency modes, such as about 200 to about 600 cm$^{-1}$, are suitable for this purpose.

The Stokes part of the Raman spectrum obtained during step 1 is referred to as $R_0(\lambda)_{s1}$, and the anti-Stokes part of the Ramnan spectrum obtained during step 1 as $R_0(\lambda)_{as1}$.

Step 2: During this step, external pressure is applied to the tissue being examined. A Raman spectrum, Stokes and anti-Stokes, is obtained by optically contacting the skin of a finger tip and the tissue/capillary bed below the skin, or another analogous section of a human body, with narrow spectral bandwidth light. The light that scatters due to the interaction of this "exciting" light with the tissue is collected and analyzed by wavelength. The exciting light has a wavelength that is absorbed by hemoglobin.

The Stokes part of the Raman spectrum obtained during step 2 is referred to as $R_p(\lambda)_{s2}$, and the anti-Stokes part of the Raman spectrum obtained during step 1 as $R_{p(\lambda)as2}$.

An objective is to effect a temperature change discernable in the Raman spectra, thereby improving detectability of the anti-Stokes components and obtaining a different form of signal modulation of Stokes components all leading to better qualitative and quantitative analysis.

One strategy is to use the Stokes features for analysis. If fluorescence or other background radiation precludes use of Stokes features, however, the following calculation can be used with the anti-Stokes components:

$$(R_0(\lambda)_{as1} - R_p(\lambda)_{as2}) = P(\lambda)C_G\sigma;$$

where $P(\lambda)$ is the incident power of the exciting light, $C_G$ is glucose concentration, and $\sigma$ is the cross-section function. If the values on the left side of the above equation are measured once to obtain a value which can be compared to an independent measurement of $C_G$, then $P(\lambda)\sigma$ can be determined, and the instrument calibrated for use in monitoring subsequent changes in $C_G$.

Subtracting the results of step 1 from step 2, Stokes or anti-Stokes, gives a number that is proportional to the concentration of glucose.

An apparatus suitable for use in this embodiment of the method is shown in FIG. 2. Light emitted by the first light source 100 passes through an amplitude modulator 230 to first and second reflectors 240, 250 such that the light joins the path of light emitted by the second light source 110. The light then irradiates the sample 200. In this particular embodiment, the first excitation wavelength is 785 nm and has a spectral bandwidth of 0.3 cm$^{-1}$. The background amplified spontaneous emission is preferably less than 1 part in $10^8$ of the 785 nm portion. If the 785 nm power is at least 100 mW at the skin surface, the Stokes glucose Raman spectral feature can be obtained in about 10 minutes.

Light scattered by the sample reaches a wavelength selection device 210 that is a wavelength selection spectrograph having a filter tuned to transmit a selected Raman feature such as 1008 nm to 1029 nm for skin keratin excited with 785 nm. The wavelength selection device 210 has a 250 $\mu$m slit and uses a holographic transmission grating. The scattered light is pre-filtered before entering the spectrograph slit using a holographic notch filter having a band blocking width of about 250 cm-l (about 1 nm) centered at 785 nm. The optical density of the filter at 785 nm is preferably at least 6 to 8. The light collection system contains no fiber optics and has an effective f number of 1.4. This can be accomplished using known optical components such as conventional 35 mm camera lenses. The focussing lenses for Raman excitation and hemoglobin absorption can be from about 2 cm to about 18 cm, depending on the size of the region to be probed.

The selected signal is then received by a detector 120. The detector 120 is a charge coupled device (CCD) array, which can be cooled with liquid nitrogen. The detector 120 can comprise a single channel detector and optionally includes spatial characteristics, such as a quadrant spatial layout, allowing simultaneous use of spatial (Hadmaard/other/tissue modulation) encoding/modulation.

The signal then passes to a phase sensitive amplifier 220 that comprises a lock-in amplifier/gated integrator set to demodulate the signal stimulated by modulator 230. The processor 130 then takes analog demodulated signal from the phase sensitive amplifier 220 and performs digitization, storage and data processing. In addition, the processor 130 can provide synchronization with concurrent tissue modulation or spatial encoding. The processor is preferably a computer.

Those skilled in the art will appreciate other variations and modifications that can be used for the method and apparatus disclosed herein.

What is claimed is:

1. A method of measuring an analyte in a tissue of a subject comprising:

(a) contacting the tissue with electromagnetic radiation having a first excitation wavelength, wherein the first excitation wavelength is sufficiently absorbed by a temperature probe within the tissue so as to increase the temperature of the temperature probe, and wherein the temperature probe and the analyte are sufficiently proximate to one another that energy deposited into one by absorption of radiation is transferred to the other so as to enhance anti-Stokes spectra scattered by the analyte;

(b) collecting the Raman spectra emitted by the tissue, wherein the Raman spectra comprise anti-Stokes spectra associated with the analyte; and (c) analyzing the collected spectra to determine a concentration of the analyte present in the tissue.

2. The method of claim 1, further comprising contacting the tissue with electromagnetic radiation having a second excitation wavelength in the near infrared region.

3. The method of claim 1, wherein the first excitation wavelength is in the near infrared region.

4. The method of claim 1, wherein the collecting further comprises substantially excluding Raman Stokes spectra emitted by the tissue.

5. The method of claim 1, wherein steps (a)–(c) are performed while the tissue is replete with blood and while the tissue is depleted of blood, and wherein the analyzing comprises determining the difference between the spectra collected in the blood replete and blood depleted states.

6. The method of claim 1, wherein the tissue is blood, ear lobe, muscle, skin, breast or brain.

7. The method of claim 1, further comprising the step of determining blood volume.

8. The method of claim 1, wherein the first excitation wavelength is about 647 to about 400 nm.

9. The method of claim 1, wherein the first excitation wavelength is about 550 to about 400 nm.

10. The method of claim 1, wherein the first excitation wavelength has a bandwidth of about 0.03 nm to about 0.000003 nm.

11. The method of claim 1, wherein the temperature probe is hemoglobin, carboxyhemoglobin, myoglobin, melanin or bilirubin.

12. The method of claim 1, wherein the analyte is glucose, urea, creatinine, pyruvate, tyrosine, tryptophan, bicarbonate, an electrolyte, lactic acid, a drug, $O_2$, $CO_2$ or NO.

13. The method of claim 1, wherein the subject is a vertebrate.

14. The method of claim 13, wherein the vertebrate is a mammal, bird, reptile or fish.

15. The method of claim 14, wherein the mammal is human, bovine, porcine, ovine, mutine, equine, canine, or feline.

16. The method of claim 1, wherein the electromagnetic radiation comprises light emitted by a laser.

17. A method of measuring an analyte in a tissue of a subject comprising:

(a) contacting the tissue with electronagnetic radiation having a first excitation wavelength in the near infrared region and a second excitation wavelength at an in isosbestic point for oxy-deoxyhemoglobin binary equilibrium, wherein the first excitation wavelength is sufficiently absorbed by a temperature probe within the tissue so as to increase the temperature of the temperature probe, and wherein the temperature probe and the analyte are sufficiently proximate to one another that energy deposited into one by absorption of radiation is transferred to the other so as to enhance anti-Stokes spectra scattered by the analyte;

(b) collecting the Raman spectra emitted by the tissue, wherein the Raman spectra comprise anti-Stokes spectra associated with the analyte; and (c) analyzing the collected spectra to determine a concentration of the analyte present in the tissue;

wherein steps (a)–(c) are performed while the tissue is replete with blood and while the tissue is depleted of blood, and wherein the analyzing comprises determining the difference between the spectra collected in the blood replete and blood depleted states and determining blood volume.

18. The method of claim 17, wherein blood volume is determined by dividing intensity of isosbestic points wavelength radiation injected into the tissue by intensity of isosbestic points wavelength radiation returned from the tissue.

19. The method of claim 17, wherein the second excitation wavelength is about 805 or about 580 nm.

* * * * *